United States Patent
Taniguchi et al.

(10) Patent No.: US 8,597,458 B2
(45) Date of Patent: Dec. 3, 2013

(54) MANUFACTURING METHOD AND A MANUFACTURING APPARATUS FOR A COMPOSITE SHEET

(75) Inventors: Hiroki Taniguchi, Kagawa (JP);
Masashi Hosokawa, Kagawa (JP);
Akane Sakai, Kagawa (JP)

(73) Assignee: Uni-charm Corporation, Ehime (JP)

( * ) Notice: Subject to any disclaimer, the term of this patent is extended or adjusted under 35 U.S.C. 154(b) by 111 days.

(21) Appl. No.: 13/258,977

(22) PCT Filed: Feb. 18, 2010

(86) PCT No.: PCT/JP2010/052406
§ 371 (c)(1),
(2), (4) Date: Nov. 22, 2011

(87) PCT Pub. No.: WO2010/109986
PCT Pub. Date: Sep. 30, 2010

(65) Prior Publication Data
US 2012/0056347 A1 Mar. 8, 2012

(30) Foreign Application Priority Data
Mar. 23, 2009 (JP) ................................ 2009-070650

(51) Int. Cl.
*B29C 41/36* (2006.01)
*B29C 41/50* (2006.01)
*A61F 13/535* (2006.01)

(52) U.S. Cl.
USPC ............ 156/276; 156/285; 156/383; 156/436

(58) Field of Classification Search
USPC ................. 156/276, 285, 383, 436; 118/308; 427/180, 197, 198
See application file for complete search history.

(56) References Cited

U.S. PATENT DOCUMENTS

| | | | | |
|---|---|---|---|---|
| 2,962,381 A | * | 11/1960 | Dobry et al. | 427/180 |
| 3,283,740 A | * | 11/1966 | Fredricksen | 118/24 |
| 3,590,981 A | | 7/1971 | Adrian | |
| 4,571,924 A | * | 2/1986 | Bahrani | 53/453 |
| 5,415,717 A | * | 5/1995 | Perneborn | 156/276 |
| 6,390,280 B1 | | 5/2002 | Boyce | |
| 7,241,358 B2 | * | 7/2007 | Gerlach | 156/276 |
| 2001/0006089 A1 | | 7/2001 | Ando et al. | |

FOREIGN PATENT DOCUMENTS

| | | |
|---|---|---|
| JP | 50-109045 A | 8/1975 |
| JP | 54-141099 A | 11/1979 |
| JP | 2001-71029 A | 6/2001 |
| JP | 2004-351803 A | 12/2004 |
| JP | 2007-050380 A | 3/2007 |

OTHER PUBLICATIONS

International Search Report from corresponding PCT application No. PCT/JP2010/052406 filed Apr. 27, 2010, 4 pgs.
Chinese Office Action from corresponding Chinese Application No. 201080013207.2 dated Dec. 28, 2012 (5 pgs).

* cited by examiner

*Primary Examiner* — Michael Tolin
(74) *Attorney, Agent, or Firm* — Brinks Gilson & Lione

(57) ABSTRACT

A manufacturing method for a composite sheet which includes: conveying a first continuous sheet in a first direction so as to abut a depressed surface of a mold member; forming an absorbent body by depositing liquid-absorbent particles on a portion of the first sheet proximal to a suction hole of the mold; and joining a second sheet over the first sheet having the absorbent body that is deposited therebetween, the second sheet being continuously transported in the first direction. A plurality of opposed slope members guide the liquid-absorbent particles onto the first sheet located on the mold member. At least one of the plurality of slope members causes the liquid-absorbent particles to reverse their falling direction from an upper slope member.

7 Claims, 6 Drawing Sheets

B-B CROSS SECTION

MANUFACTURING METHOD AND A MANUFACTURING APPARATUS FOR A COMPOSITE SHEET

RELATED APPLICATION

The present application is a 35 U.S.C. §371 national stage filing of International Patent Application No. PCT/JP2010/052406, filed Feb. 18, 2010, to which priority is claimed under 35 U.S.C. §120 and through which priority is claimed under 35 U.S.C. §119 to Japanese Priority Patent Application No. 2009-070650, filed Mar. 23, 2009.

TECHNICAL FIELD

The invention relates to a manufacturing method and a manufacturing apparatus for a composite sheet associated with an absorbent article of a disposable diaper etc.

BACKGROUND ART

As an example of an absorbent article to absorb liquid such as exudates, a disposable diaper, a sanitary napkin and the like are used. These absorbent articles include generally an absorbent body obtained by forming pulp fibers into a predetermined shape. However, recently, it is being considered that an absorbent body is configured without using liquid absorbent fibers such as pulp fibers, by using particulate superabsorbent polymers (hereinafter referred to as SAP). In this case, the absorbent body is used in a manner of a composite sheet. That is, a composite sheet is manufactured which is formed by sandwiching the absorbent body between a first sheet and a second sheet, the absorbent body being made of the particulate SAP.

As a technique for manufacturing such a composite sheet, Patent Literature 1 discloses that a sliding plate is used when the absorbent body is formed by dropping the SAP onto a sheet which is continuous in a transporting direction. That is, in the course of sliding on the sliding plate, the SAP is distributed in a width direction of a sheet; thereby, trying to make the deposit distribution of the SAP on the sheet even in the width direction.

CITATION LIST

[Patent Literature].
[PTL 1] Japanese Patent Application Laid-open Publication No. 2007-50380

SUMMARY OF THE INVENTION

Technical Problem

It is expected that the longer the sliding-path length that the SAP slides on the sliding plate, the more evenly the deposit of the SAP is distributed in the width direction. However, in order to lengthen the sliding-path length, it is necessary to employ a long sliding plate, which results in a large-sized apparatus.

This invention has been made in view of the above problems, and an advantage thereof is to provide a manufacturing method and a manufacturing apparatus for a composite sheet which enables the deposit distribution of the liquid-absorbent particles such as of the SAP to be even in the width direction without making the manufacturing apparatus bigger.

Solution to Problem

An aspect of the invention to achieve the above advantage is a manufacturing method for a composite sheet formed by sandwiching an absorbent body that absorbs liquid between a first sheet and a second sheet, including:

conveying the first sheet with abutting a mold member on a surface of the mold member, the first sheet being continuous in a first direction, the mold member including a mold formed on the surface in a depressed shape and moving along the first direction perpendicular to a width direction of the surface;

forming the absorbent body using a procedure in which a liquid-absorbent particle falls towards the first sheet abutting the surface and the liquid-absorbent particle is deposited on a corresponding portion of the first sheet to the mold by suction from a suction hole of the mold; and joining the second sheet and the first sheet with placing the second sheet over the first sheet, the first sheet having the absorbent body that is deposited thereon, the second sheet being continuously transported in the first direction, wherein in the forming, a plurality of slope members having a slope is included in an up-and-down direction, a height of an upstream end of the slope and a height of a downstream end of the slope are different in the first direction, while the liquid-absorbent particle successively slides a slope of the plurality of slope members, the liquid-absorbent particle is distributed in the width direction and falls on the first sheet located on the mold member, at least one slope member of the plurality of slope members makes the liquid-absorbent particle reverse its sliding direction and slide, the liquid-absorbent particle falling from a slope member adjacent above the one slope member.

Further, a manufacturing apparatus for a composite sheet formed by sandwiching an absorbent body that absorbs liquid between a first sheet and a second sheet, including:

a mold member that includes a mold formed on a surface in a depressed shape, that moves along a first direction perpendicular to a width direction of the surface, and that conveys the first sheet with the first sheet abutting on the surface, the first sheet being continuous in the first direction;

a liquid-absorbent-particle-supply mechanism that drops and supplies the liquid-absorbent particle towards the first sheet abutting the surface;

a suction mechanism that sucks air from a suction hole in the mold in order to form the absorbent body by depositing the liquid-absorbent particle on a corresponding portion of the first sheet to the mold; and a joining mechanism that places the second sheet over the first sheet on which the absorbent body is deposited and joins the sheets, the second sheet being continuously transported along the first direction, wherein the liquid-absorbent-particle-supply mechanism includes in an up-and-down direction a plurality of slope members having a slope, a height of an upstream end of the slope and a height of a downstream end of the slope are different from each other in the first direction, while the liquid-absorbent particle successively slides a slope of the plurality of slope members, the liquid-absorbent particle is distributed in the width direction and falls onto the first sheet on the mold member, at least one slope member of the plurality of slope members makes the liquid-absorbent particle reverse its sliding direction and slide, the liquid-absorbent particle falling from a slope member adjacent above the one slope member.

Other features of this invention will become apparent from the description in this specification and the attached drawings.

Effects of the Invention according to the invention, it is possible to makes the deposit distribution of the liquid-absorbent particles such as SAP even in the width direction without making the manufacturing apparatus bigger.

MODE FOR CARRYING OUT THE INVENTION

Figures 1A, 1B:
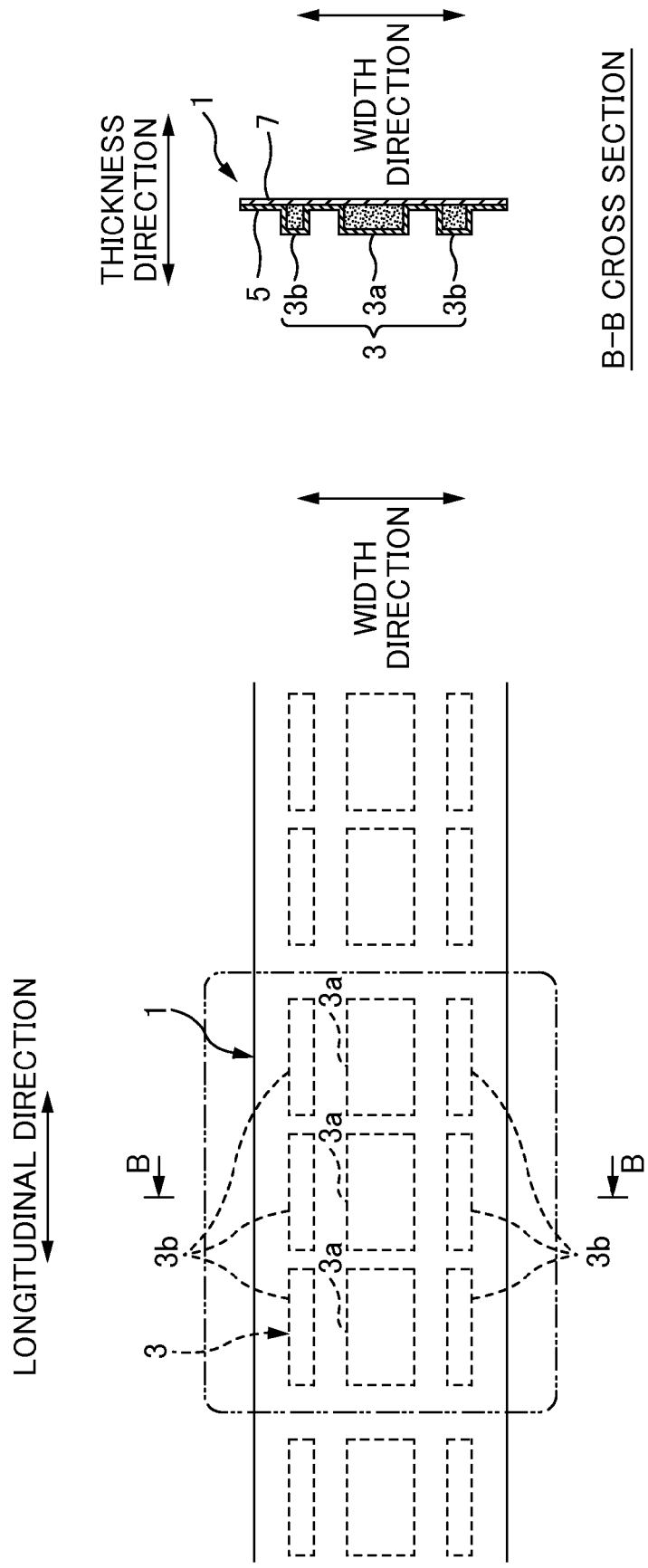
FIG. 1A is a plan view of an absorbent main body 1 of a disposable diaper.
FIG. 1B is cross-sectional view taken along the line B-B in FIG. 1A.

At least the following matters will be made clear by the description in the present specification and the accompanying drawings.

A manufacturing method for a composite sheet formed by sandwiching an absorbent body that absorbs liquid between a first sheet and a second sheet, including:

conveying the first sheet with abutting a mold member on a surface of the mold member, the first sheet being continuous in a first direction, the mold member including a mold formed on the surface in a depressed shape and moving along the first direction perpendicular to a width direction of the surface;

forming the absorbent body using a procedure in which a liquid-absorbent particle falls towards the first sheet abutting the surface and the liquid-absorbent particle is deposited on a corresponding portion of the first sheet to the mold by suction from a suction hole of the mold; and joining the second sheet and the first sheet with placing the second sheet over the first sheet, the first sheet having the absorbent body that is deposited thereon, the second sheet being continuously transported in the first direction, wherein in the forming, a plurality of slope members having a slope is included in an up-and-down direction, a height of an upstream end of the slope and a height of a downstream end of the slope are different in the first direction, while the liquid-absorbent particle successively slides a slope of the plurality of slope members, the liquid-absorbent particle is distributed in the width direction and falls on the first sheet located on the mold member, at least one slope member of the plurality of slope members makes the liquid-absorbent particle reverse its sliding direction and slide, the liquid-absorbent particle falling from a slope member adjacent above the one slope member.

In such a manufacturing method for a composite sheet, at least one slope member makes the liquid-absorbent particle reverse its sliding direction, the liquid-absorbent particle falling from an adjacent slope member above it. And, the slope member makes the particle slide on a slope thereof. This makes it possible to lengthen the sliding-path length of the liquid-absorbent particle without making the manufacturing apparatus bigger in the first direction. Because of making the sliding-path length lengthen, the liquid-absorbent particle can be distributed evenly in the width direction. As a result thereof, the even deposit distribution of the liquid-absorbent particles in the width direction can be achieved.

Further, because of reversing the sliding direction of the liquid-absorbent particle in conjunction with falling from the slope member, the liquid-absorbent particle is likely to be distributed. This also makes it possible to achieve the even deposit distribution of the liquid-absorbent particles in the width direction.

In such a manufacturing method for a composite sheet, desirably three or more of the slope members are included, and
concerning all of the slope members, sliding directions of slope members adjacent in the up-and-down direction are opposite from each other.

In such a manufacturing method for a composite sheet, under the condition in which the size of the manufacturing apparatus is restricted in the first direction, it is possible for sliding-path length of the liquid-absorbent particle to be longest. Further, the number of times the sliding direction is reversed in conjunction with falling is maximized. Therefore, the liquid-absorbent particle is more likely to be distributed evenly in the width direction.

In such a manufacturing method for a composite sheet, desirably the mold of the mold member is formed at a predetermined interval in the first direction, a lowermost slope member, of the plurality of slope members, drops the liquid-absorbent particle towards the first sheet located on the mold member, in terms of the component along a horizontal direction, a sliding direction of the lowermost slope member is the same as a moving direction in which the mold member is moving at a landing position of the liquid-absorbent particle on the first sheet.

Such a manufacturing method for a composite sheet can prevent the uneven deposit distribution of the absorbent body in the first direction. The detail is as follows. The mold member moves in the first direction. Therefore, the liquid-absorbent particle is generally more likely to be deposited on the upstream side end of the mold in the first direction; that is, concerning the deposit distribution of the absorbent body, the deposit tends to be thicker on the upstream than on the downstream in the first direction. Concerning this point, if the sliding direction of the lowermost slope member is aligned with the moving direction of the mold member, the moving speed of the mold member with respect to the liquid-absorbent particles can be relatively slower. As a result thereof, it is possible to prevent an excess deposit on the upstream side of the mold, which prevents the uneven distribution of the deposit in the first direction.

In such a manufacturing method for a composite sheet, desirably the mold member is a rotating drum continuously rotating in a rotating direction that is one direction of circumferential directions and is the first direction, the rotating drum transports the first sheet with wrapping the sheet around an outer circumferential face at a predetermined wrapping angle, the outer circumferential face serving as the surface, the mold is formed in a depressed shape on the outer circumferential face at a regular interval in the rotating direction, a lower end of the lowermost slope member of the plurality of slope members is positioned, in the horizontal direction, at a top of the outer circumferential face of the rotating drum, or on a downstream side from the top in the rotating direction.

Such a manufacturing method for a composite sheet can prevent the uneven deposit distribution of the absorbent body in the rotating direction of the rotating drum. The detail is as follows. The rotating drum rotates in the rotating direction. Therefore, the liquid-absorbent particle is generally more likely to be deposited on the upstream side end of the mold in the rotating direction; that is, concerning the deposit distribution of the absorbent body, the deposit tends to be thicker on the upstream than on the downstream in the rotating direction. Concerning this point, if the lower end of the lowermost slope member is located as mentioned above, the landing position of the liquid-absorbent particle is on the more downstream side of the rotating direction than the top of the outer circumferential face of the rotating drum, the landing position being a position at which the liquid-absorbent particle scattered from the lower end is landed on the rotating drum. Thus, the landed liquid-absorbent particle becomes likely to flow downstream because of a slope of the outer circumferential face, which is inclined to the downstream side. This results in preventing an excess deposit on the upstream side of the mold in the rotating direction.

In such a manufacturing method for a composite sheet, desirably a slope of a slope member that receives the liquid-absorbent particle falling from a slope member adjacent above that slope member is arranged astride a lower end of the adjacent slope member in the first direction.

In such a manufacturing method for a composite sheet, all liquid-absorbent particles falling from the slope member adjacent above that slope member can be received.

In such a manufacturing method for a composite sheet, desirably on a slope of the lowermost slope member of the plurality of slope members, a plurality of guiding grooves along the sliding direction are formed lined up in the width direction, a position of a lower end of the guiding groove in the width direction is within the mold.

In such a manufacturing method for a composite sheet, the liquid-absorbent particle is guided by the guiding groove and is definitely led to the mold. Therefore, the amount of the liquid-absorbent particles that are deposited outside the mold can be reduced considerably.

In such a manufacturing method for a composite sheet, desirably in the forming, a box member that forms a partitioned space together with the surface is included, in the box member, the plurality of slope members are housed and a discharging member that discharges the liquid-absorbent particle is housed above the plurality of slope members, both ends of the plurality of slope members in the width direction are fixed on a wall of the box member.

In such a manufacturing method for a composite sheet, it is difficult for the air to pass between the both edges of the slope members in the width direction and an inner wall of the box member. Therefore, an airflow which is flowing from the discharging member of the box member to the suction holes of the mold can be concentrated in the sliding direction of the liquid-absorbent particle, which results in a stable sliding of the liquid-absorbent particle.

In such a manufacturing method for a composite sheet, desirably on a downstream side in the sliding direction of the lowermost slope member of the plurality of slope members, a wall is not arranged, the wall being hit by the liquid-absorbent particle that falls from the lowermost slope member and has not landed on the first sheet located on the mold member yet.

In such a manufacturing method for a composite sheet, the foregoing wall is not arranged. Therefore, without disturbing the state in which the liquid-absorbent particle is distributed substantially evenly by sliding on the slope member, the liquid-absorbent particle falls from the slope member and lands on the first sheet. This can make the deposit distribution of the absorbent body even in the width direction.

Further, a manufacturing apparatus for a composite sheet formed by sandwiching an absorbent body that absorbs liquid between a first sheet and a second sheet, including:

a mold member that includes a mold formed on a surface in a depressed shape, that moves along a first direction perpendicular to a width direction of the surface, and that conveys the first sheet with the first sheet abutting on the surface, the first sheet being continuous in the first direction;

a liquid-absorbent-particle-supply mechanism that drops and supplies the liquid-absorbent particle towards the first sheet abutting the surface;

a suction mechanism that sucks air from a suction hole in the mold in order to form the absorbent body by depositing the liquid-absorbent particle on a corresponding portion of the first sheet to the mold; and a joining mechanism that places the second sheet over the first sheet on which the absorbent body is deposited and joins the sheets, the second sheet being continuously transported along the first direction, wherein the liquid-absorbent-particle-supply mechanism includes in an up-and-down direction a plurality of slope members having a slope, a height of an upstream end of the slope and a height of a downstream end of the slope are different from each other in the first direction, while the liquid-absorbent particle successively slides a slope of the plurality of slope members, the liquid-absorbent particle is distributed in the width direction and falls onto the first sheet on the mold member, at least one slope member of the plurality of slope members makes the liquid-absorbent particle reverse its sliding direction and slide, the liquid-absorbent particle falling from a slope member adjacent above the one slope member.

In such a manufacturing apparatus for a composite sheet, at least one slope member makes the liquid-absorbent particle reverse its sliding direction, the liquid-absorbent particle falling from an adjacent slope member above it. And, the slope member makes the particle slide on a slope thereof. This makes it possible to lengthen the sliding-path length of the liquid-absorbent particle without making the manufacturing apparatus bigger in the first direction. Because of making the sliding-path length lengthen, the liquid-absorbent particle can be distributed evenly in the width direction. As a result thereof, the even deposit distribution of the liquid-absorbent particle in the width direction can be achieved.

Further, because of reversing the sliding direction of the liquid-absorbent particle in conjunction with falling from the slope member, the liquid-absorbent particle is more likely to be distributed. This also makes it possible to achieve the even deposit distribution of the liquid-absorbent particle in the width direction.

PRESENT EMBODIMENT

A manufacturing method and manufacturing apparatus for a composite sheet according to the present embodiment is used for manufacturing an absorbent main body 1 (corresponding to a composite sheet) of a disposable diaper, for example.

FIGS. 1A and 1B are explanatory diagrams of the absorbent main body 1 of a disposable diaper. FIG. 1A is a plan view, and FIG. 1B is a cross-sectional view taken along the line B-B in FIG. 1A. In FIG. 1A, a unit corresponding to a diaper product is shown by surrounding it by double-dotted chained line.

The absorbent main body 1, among a plurality of components of a disposable diaper, corresponds to a component which comes into contact with the crotch of the wearer to absorb exudates such as urine etc. When viewed in a planar view, the absorbent main body 1 has a substantially rectangular shape having a longitudinal direction and a width direction. In a thickness direction, an absorbent body 3 to absorb liquid is covered with a surface sheet 5 from the surface side, which is the human-body side; the absorbent body 3 is also covered with a back face sheet 7 from the back face side, which is the opposite side. And, in a state of sandwiching the absorbent body 3 between these surface sheet 5 and back face sheet 7, the surface sheet 5 and the back face sheet 7 are attached to each other in a frame-like manner at portions extending outwardly beyond four sides of the absorbent body 3.

The surface sheet 5 and back face sheet 7 are a liquid-permeable sheet; for example, nonwoven fabric made of synthetic fiber etc having a basis weight of 10 to 50 (g/m$^2$). As a synthetic fiber, single fiber or conjugated fiber having a sheath-core structure such as polyethylene, polyethylene terephthalate etc can be provided for example. The back face sheet 7 may be a liquid-impermeable sheet.

The absorbent body 3 is made of particulate superabsorbent polymers having a particle diameter of 100 to 800 micrometer (corresponding to a liquid-absorbent particle, hereinafter referred to as SAP), and is formed by depositing the SAP at a basis weight of 100 to 500 (g/m$^2$). The absorbent body 3 is configured by a plurality of island-shaped deposited portions 3a, 3b into which the absorbent body 3 is divided in a predetermined depositing pattern in the longitudinal direction and width direction. In the example shown in the figures, the absorbent body 3 is divided into three parts in each of the width direction and longitudinal direction. The absorbent body 3 includes a total of nine deposited portions 3a, 3b. Since the width direction corresponds to the left-and-right direction of a human body, the body 3 is divided symmetrically into a plurality of portions relative to the center line of that width direction. The deposited portions 3a located at the center are set to be wider in width than the deposited portions 3b located at the both ends thereof. As a specific example of SAP, UG-840D (product of Sumitomo Seika Chemicals Co., Ltd.) etc is provided.

Figure 2:
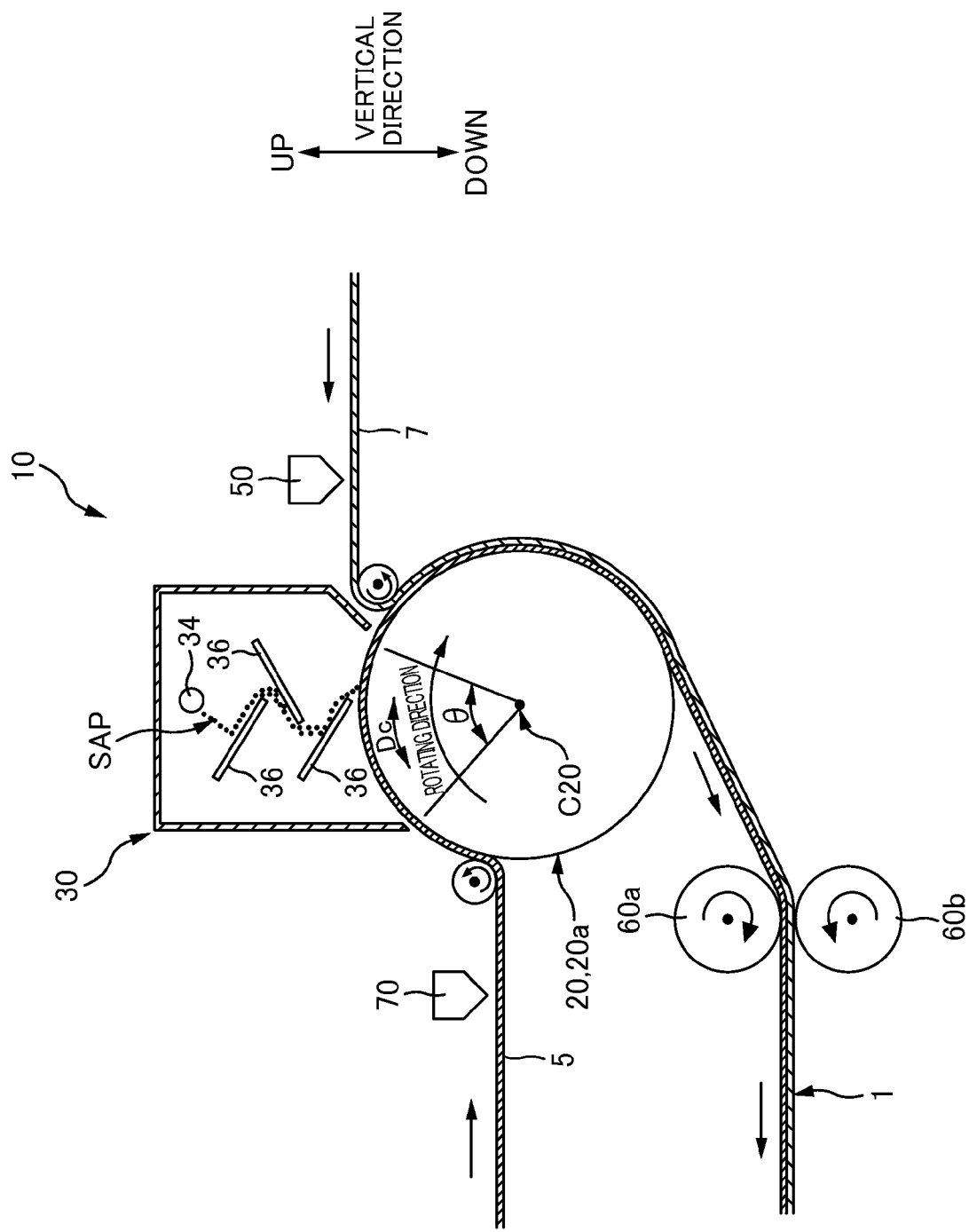
FIG. 2 is a schematic side view of a manufacturing apparatus 10 for the absorbent main body 1.

FIG. 2 is a schematic side view of the manufacturing apparatus 10 for the absorbent main body 1. At the point of this process in the course of manufacturing, in the same way as FIG. 1A, the absorbent main body 1 is a continuous body that has not yet been divided into a product unit in the longitudinal direction. Further, the width direction of the absorbent main body 1 is aligned in the width direction of the manufacturing apparatus 10 (a direction perpendicular to the paper surface in FIG. 2). Hereinafter this direction is referred to as merely the "width direction". In this regard, the width direction is horizontal.

This manufacturing method includes: (1) a conveying step (corresponding to "conveying") in which the surface sheet 5 (corresponding to a first sheet) is conveyed with wrapping the sheet 5 around the outer circumferential face 20a of the rotating drum 20 at a predetermined wrapping angle, the surface sheet 5 being continuous in the outer circumferential face 20a of a rotating drum 20, the rotating drum 20 rotating continuously along a rotating direction (corresponding to a first direction) that is one direction of the circumferential direction Dc; (2) a forming step (corresponding to "forming") in which the absorbent body 3 is formed using a procedure in which a SAP-supply device 30 drops and supplies the SAP towards the surface sheet 5 wrapped around the outer circumferential face 20a of the rotating drum 20 and the SAP is deposited on a corresponding portion of the surface sheet 5 to a mold 21 by suction from the suction holes of the mold, the mold being formed in a depressed shape on the outer circumferential face 20a of the rotating drum 20; and (3) a joining step (corresponding to "joining") in which the back face sheet 7 (corresponding to a second sheet) is placed over the surface sheet 5 having the absorbent body 3 that is deposited thereon and the sheets are joined and integrated, the back face sheet 7 being continuously transported in the circumferential direction Dc.

Figure 3:
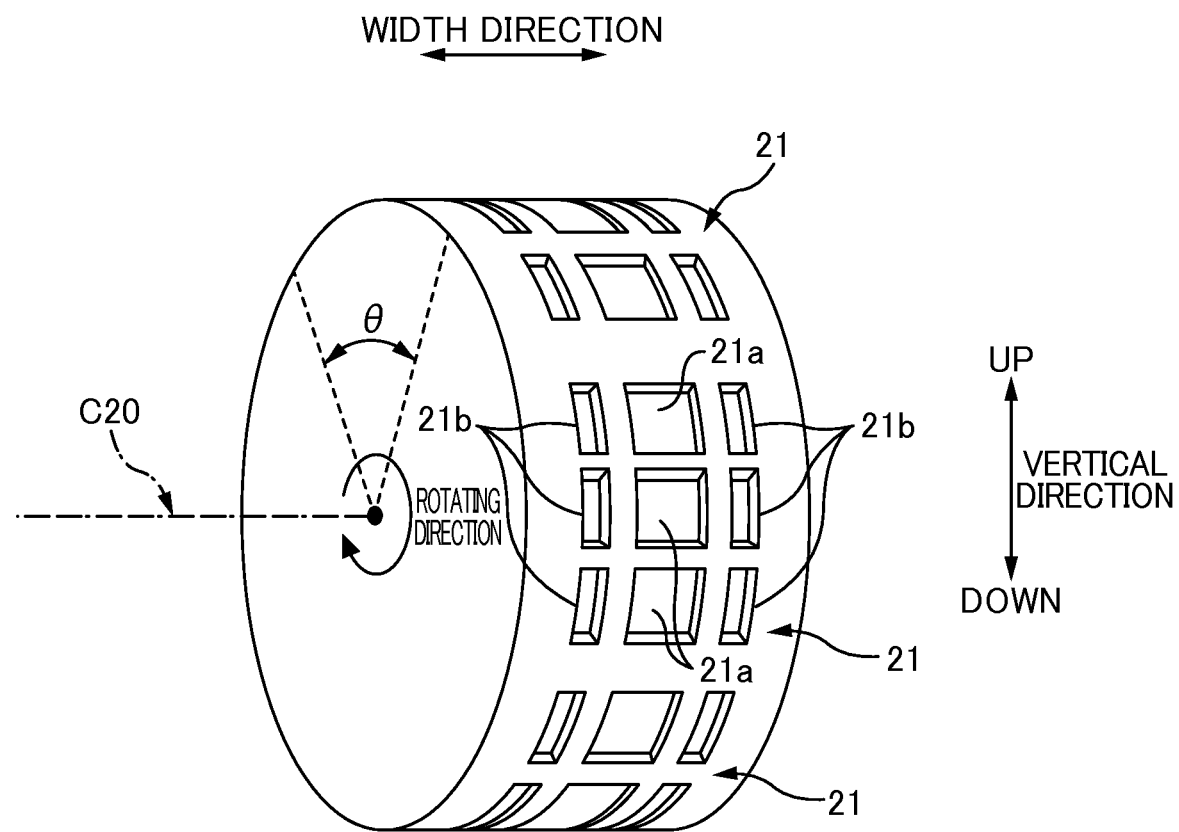
FIG. 3 is a perspective view of a rotating drum 20.

FIG. 3 is a perspective view of the rotating drum 20. The main body of the rotating drum 20 (corresponding to a mold member) is a cylinder that is driven and rotates about a horizontal axis C20 along the width direction. As shown in FIG. 3, the outer circumferential face 20a (corresponding to a surface) of the rotating drum 20 is horizontal with respect to the width direction. On the outer circumferential face 20a, the molds 21 of the absorbent body 3 are disposed in a depressed shape at a regular interval in the circumferential direction Dc. Each mold 21 is formed based on the foregoing depositing pattern; that is, each one of the molds 21 includes nine depressions 21a, 21b in the example shown in the figures. A bottom section of each of the depressions 21a, 21b is formed horizontally in the width direction, and a large number of suction holes (not shown) are formed thereon. These suction holes are configured to suck the air in the span of the rotation angle range θ of the rotating drum 20, the rotation angle range θ corresponding to at least the foregoing forming step. Thereby, in forming step of FIG. 2, SAP is deposited selectively on a corresponding portion of the surface sheet 5 to each of the depressions 21a, 21b of the mold 21.

An example of a suction mechanism that makes the suction holes suck the air in the rotation angle range θ is as follow: having suction holes as through holes which communicate with an inner circumferential space of the rotating drum 20; including a partition wall which partitions a corresponding space of the inner circumferential space to the rotation angle range θ; and connecting a negative pressure source such as a blower to the space in order to suck the air from the space.

Figure 4A:
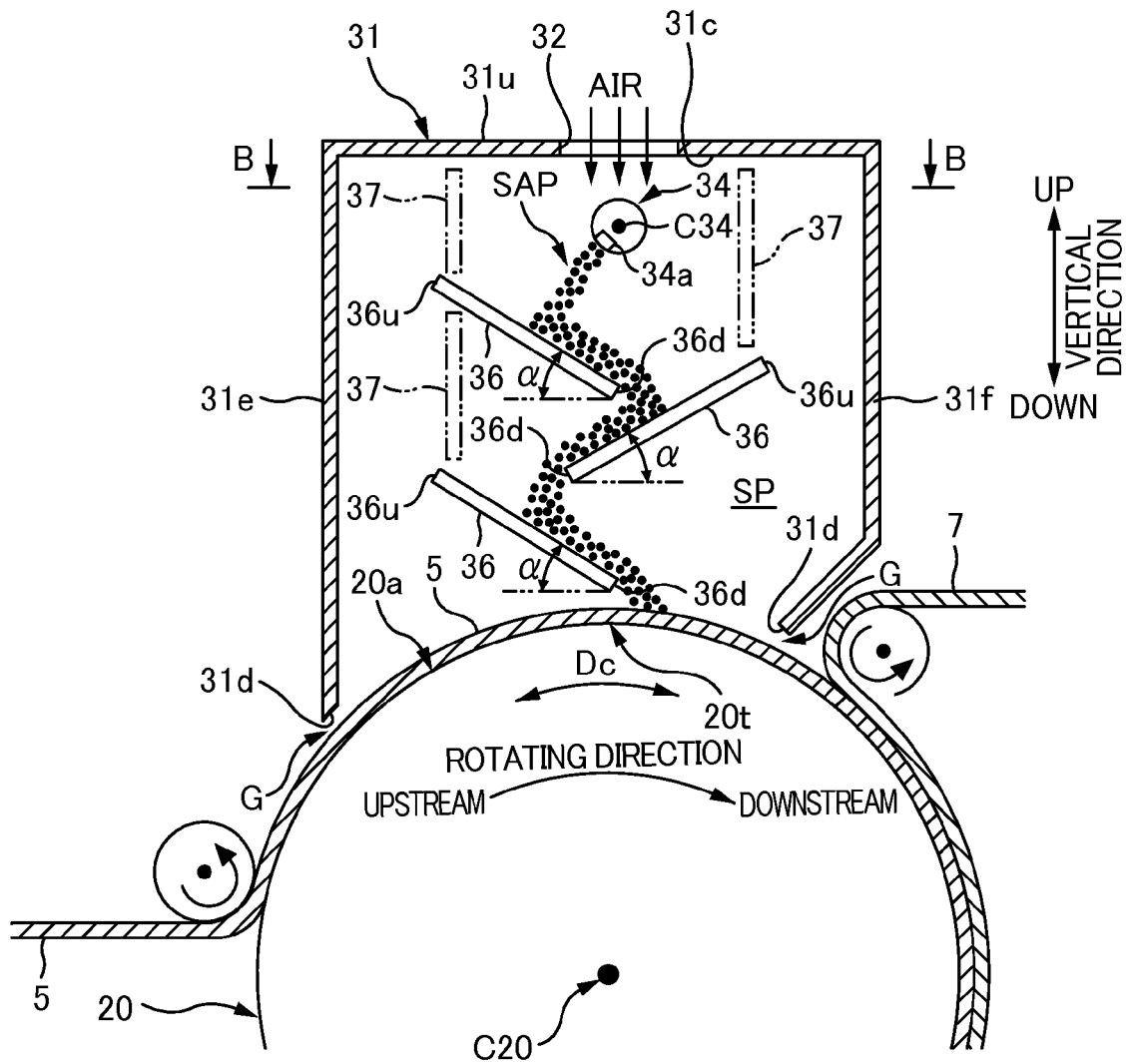
FIG. 4A is a magnified view of a SAP-supply device 30.
Figure 4B:
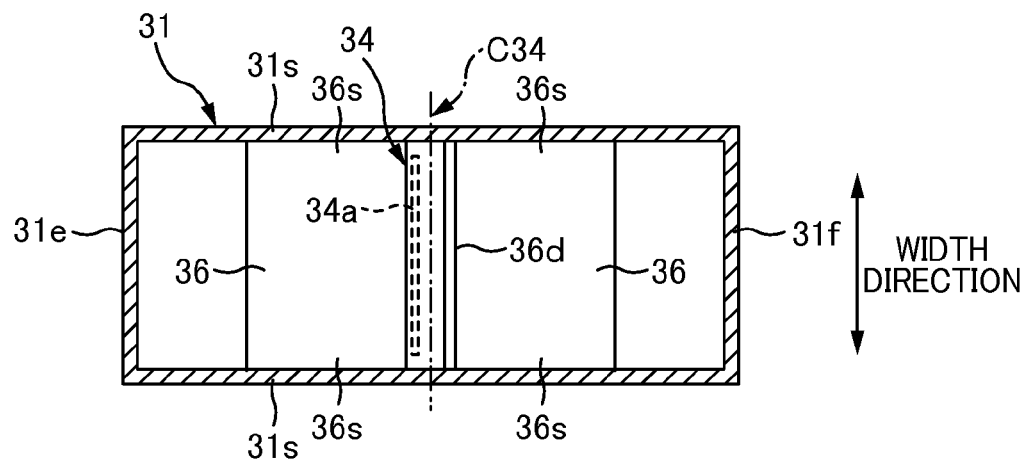
FIG. 4B is a cross-sectional view taken along the line B-B in FIG. 4A.

FIG. 4A is a magnified view of the SAP-supply device 30, and FIG. 4B is a cross-sectional view taken along line B-B in FIG. 4A. The SAP-supply device 30 (corresponding to a liquid-absorbent-particle-supply mechanism) is placed above a top 20t of the outer circumferential face 20a of the rotating drum 20. The SAP-supply device 30 includes: a box member 31 which, together with that outer circumferential face 20a, forms a space SP located above the outer circumferential face 20a into a substantially closed space; a SAP-discharging pipe 34 which is housed in the box member 31 and discharges the SAP; and a plurality of sliding plates 36 which receive and distribute the SAP in the width direction while sliding of the SAP, the SAP being discharged and falling from the SAP-discharging pipe 34.

The box member 31 is, for example, a substantially rectangular parallelepiped lacking only a lower side wall, and include five walls except the lower side wall. The box member 31 is arranged with its lower surface being opposite the top 20t of the outer circumferential face 20a of the rotating drum 20. Therefore, being surrounded by the box member 31 prevents effectively SAP from scattering away.

Further, on a wall 31u of the box member 31 in the upper surface side, an air-inlet opening 32 is formed completely through the wall. Therefore, the air sucked from the suction holes of the foregoing mold 21 is entered from the air-inlet opening 32 into the box member 31. This results in reducing an amount of the air which intrudes inside the box member 31 from a gap G between a lower end 31d of the box member 31 and the outer circumferential face 20a of the rotating drum 20. This effectively prevents disorder of the SAP in a falling direction or landing position, the SAP falling from the lower end 36d of the sliding plate 36 to the surface sheet 5 that is located on the rotating drum 20.

This air-inlet opening 32 is preferably formed on a portion which is on the wall 31u on the upper surface side and is right above the SAP-discharging pipe 34, as shown in FIG. 4A. This enables the air entered from the air-inlet opening 32 to concentrate on the SAP located on the sliding plate 36, which results in stable sliding of the SAP.

Further, the opening area of the air-inlet opening 32 is preferably set to be larger than or equal to the total area of the gaps G that is between the lower end 31d of the box member 31 and the outer circumferential face 20a of the rotating drum 20. This can prevent intrusion of the air from the gap G more definitely. In this regard, in the case of the box member 31, as shown in FIGS. 4A and 4B, the downstream end 31d of the box member 31 is formed by four walls: walls 31e, 31f that the box member 31 includes in the upstream side and downstream side; and a pair of side walls 31s, 31s in the width direction. Each of these walls 31e, 31f, 31s, and 31s have one gap G. Therefore, the foregoing "total area of the gaps G" is calculated as the total area of these four gaps G.

The SAP-discharging pipe 34 (corresponding to a discharging member) is a pipelike member such as a round pipe. The SAP-discharging pipe 34 is arranged above in the box member 31, and a pipe axis C34 of the pipe 34 is aligned with the width direction. On a pipe wall (peripheral wall), a slit-shaped discharge opening 34a along the width direction is formed completely through the wall. Inside the pipe, a helical screw feeder (not shown), which is for transporting the SAP in the width direction, is disposed and a rotational-axis direction thereof is aligned with the width direction. Further, at one end of the pipe ends of the SAP-discharging pipe 34, the SAP is continuously supplied from the SAP supply source through suitable pipelines. Therefore, by rotation of the helical screw feeder, the SAP is transported from the one end of the pipe ends to the other pipe end in the SAP-discharging pipe 34. While transporting, the SAP is discharged at each position in the width direction from the discharge opening 34a. Therefore, the SAP is discharged from the discharge opening 34a in the form of a curtain throughout the width direction.

A plurality of sliding plates 36 (corresponding to a plurality of slope members) are disposed side by side below the SAP-discharging pipe 34 in a multilayered manner (three in the figures) in the up-and-down direction, with their positions differing in height. Therefore, the SAP which is discharged by the SAP-discharging pipe 34 successively slides on the inclined upper surfaces (corresponding to slopes) of these sliding plates 36 from an upper sliding plate 36 via a middle sliding plate 36 to a lower sliding plate 36. Thereafter, from the lower end of the lower sliding plate 36, the SAP is scattered in the form of a curtain throughout the width direction toward the surface sheet 5 located on the outer circumferential face 20a of the rotating drum 20.

Each of the sliding plates 36 is a rectangular plate whose upper surface is flat, for example. The upper surface is arranged horizontally in the width direction, in order to achieve even distribution of the SAP in the width direction. In the circumferential direction Dc, the upper surface is inclined with respect to the horizontal. In other words, the height of the upper surface at upstream end 36u (36d) in the rotating direction is different from the height at downstream end 36d (36u). Therefore, the SAP slides in a direction parallel to the circumferential direction Dc as the sliding direction. However, there are two circumferential directions Dc: that is, a forward direction which is along the rotating direction of the rotating drum 20, and the opposite direction. The direction of inclination of each sliding plate 36 decides the sliding direction of the SAP on that sliding plate 36.

In the example of FIG. 4A, concerning all sliding plates 36, the directions of inclination of a pair of sliding plates 36, 36 adjacent in the up-and-down direction are opposite to each other. Therefore, the sliding directions of the sliding plates 36 arranged in a multilayered manner in the up-and-down direction are in staggered arrangement. That is, on the middle sliding plate 36, the SAP reverses its sliding direction and slides, the SAP falling from a lower end 36d of the upper sliding plate 36 adjacent above it. On the lower sliding plate 36, the SAP reverses its sliding direction and slides, the SAP falling from a lower end 36d of the middle sliding plate 36 adjacent above it.

According to the arrangement of the sliding plates whose directions are opposite, while avoiding making the manufacturing apparatus 10 bigger, the SAP can be distributed evenly in the width direction. A more specific description will be made below.

In order to distribute evenly particulate the SAP in the width direction, it is effective to lengthen a sliding-path length that the SAP rolls. However, in this case, a long sliding plate 36 is needed, which results in making the manufacturing apparatus 10 bigger. In terms of this, in the case of reversing the sliding direction by setting to be opposite inclinations of the pair of sliding plates 36, 36 adjacent in the up-and-down direction as mentioned above, sticking a plurality of sliding plates 36, 36 makes it possible to achieve a sufficiently long sliding-path length using short sliding plates 36. This can prevent the manufacturing apparatus 10 from becoming bigger in size.

An angle of inclination α of the upper surface of the sliding plate 36 with respect to the horizontal is selected within the range of angle greater than 0° and smaller than 90°. In the example shown in the figures, the inclination α of all sliding plates 36 is 30°. However, the inclination α may be different from each other.

Further, in the example shown in the figures, the lower end 36d of each sliding plate 36 is located at the same position in the circumferential direction Dc throughout the width direction (see FIG. 4B). This enables the landing position of the SAP falling from the lower end 36d to be organized throughout the width direction. As a result, disorder of the distribution of the SAP in the width direction, which is caused in conjunction with the falling, is suppressed.

Further, in the example shown in the figures, between the sliding plates 36, 36 adjacent in the up-and-down direction, the upper surface of the lower sliding plate 36 is arranged astride the lower end 36d of the upper sliding plate 36 in the rotating direction. This enables the lower sliding plate 36 to receive all of the SAP falling from the upper sliding plate 36 definitely. This can prevent effectively the SAP from being deposited disorderly, the SAP leaking and reaching the outer circumferential face 20a of the rotating drum 20.

As shown in FIG. 4B, both edges 36s, 36s of each sliding plate 36 in the width direction abut and are fixed to the pair of side walls 31s, 31s (corresponding to walls) without any gap, the side walls being included by the box member 31 at both ends in the width direction. Thereby, it becomes difficult for the air to pass between the both edges 36s, 36s of each sliding plate 36 and an inner wall of the box member 31. As a result, an airflow can be concentrated in the sliding direction of the SAP, the airflow flowing from a position of the SAP-discharging pipe 34 of the box member 31 to the suction holes of the mold 21. This results in stable sliding of the SAP.

In order to increase this effect of stabilization, as shown with the double-dotted chained line in FIG. 4A, it is preferable to close the space by placing vertical walls 37 between an upper edge 36u of each sliding plate 36 and an upper edge 36u of the sliding plate 36 adjacent above that sliding plate 36 or between the upper edge 36u of each sliding plate 36 and a ceiling 31c of the box member 31. This enables the foregoing airflow to be more stable. Further, scattering of the SAP can also be prevented; as a result, it is possible to effectively prevent the SAP from being deposited at any position other than the depressions 21a, 21b of the mold 21. In this regard, it is not necessary to place the foregoing vertical walls 37 concerning all of the sliding plates. Placing the walls for just any one of sliding plates 36 will have a reasonable effect.

Further, in the example shown in the figures, in terms of the component along the horizontal direction, the sliding direction of lower sliding plate 36 is the same as the rotating direction (forward direction) of the rotating drum 20 at the SAP landing position on the surface sheet 5. This is for preventing uneven deposit distribution of the absorbent body 3 in the circumferential direction Dc.

Figure 5A:
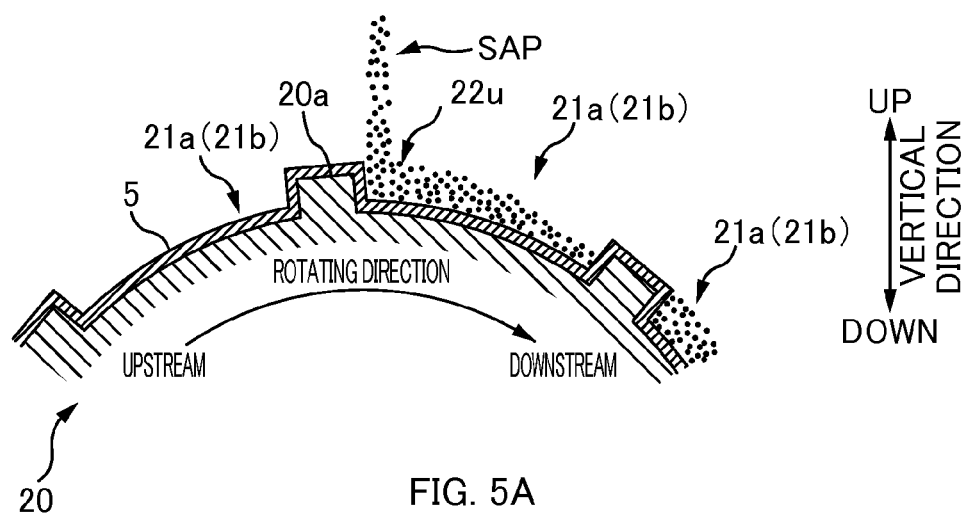
FIGS. 5A to 5C are explanatory diagrams showing a method for preventing the uneven deposit distribution of an absorbent body 3 in the circumferential direction Dc.
Figure 5B:
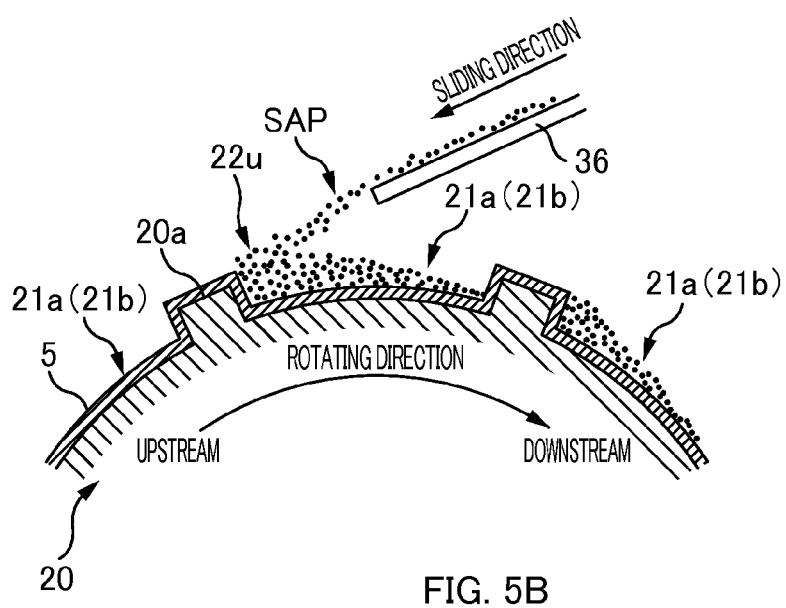
Figure 5C:
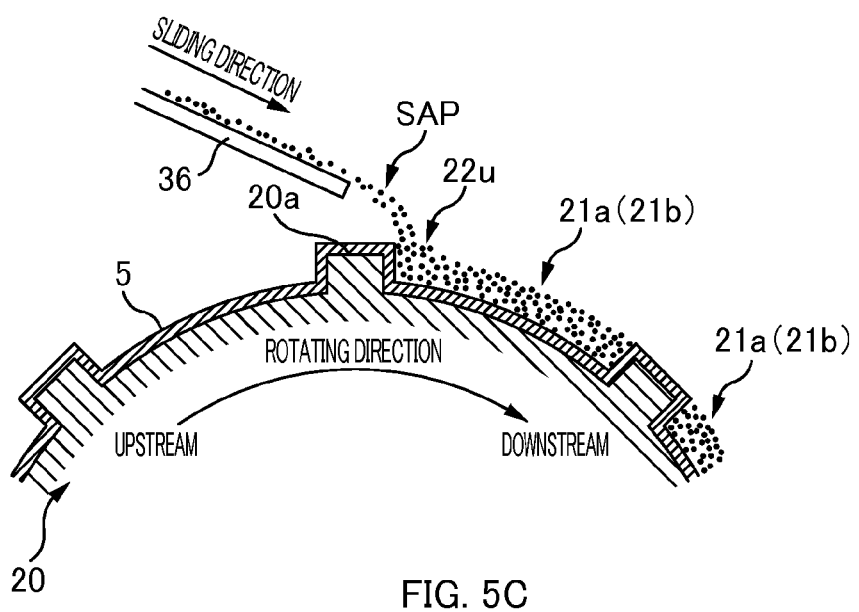

FIG. 5A shows an explanatory diagram thereof. The rotating drum 20 rotates in the rotating direction. Therefore, in a case of dropping SAPs vertically for example, SAP is likely to roll on the upstream side of the depression 21a (21b) of the mold 21 in the rotating direction and to accumulate on an edge 22u on the upstream side. That is, the deposit distribution of the absorbent body 3 tends to be thicker on the upstream than on the downstream in the rotating direction. Concerning this point, if, as shown in the reference example of FIG. 5B, the sliding direction of the lower sliding plate 36 is set to be opposite to the rotating direction of the rotating drum 20, the rotational speed of the rotating drum 20 with respect to the SAP increases relatively. This encourages the deposit of the SAP on the upstream side mentioned above. As opposed thereto, if the sliding direction of the lower sliding plate 36 is the same as the rotating direction (forward direction) of the rotating drum 20 as shown in FIG. 5C, the rotational speed of the rotating drum 20 with respect to the SAP can lower relatively. This prevents the deposit on the upstream side of the depression 21a (21b) of the mold 21, which results in preventing the uneven deposit distribution in the circumferential direction Dc.

Further, in terms of preventing the uneven deposit distribution in the circumferential direction Dc, in the example of FIG. 4A, the lower end 36d of the lower sliding plate 36 is positioned, in the horizontal direction, at the top 20t (the highest position) of the outer circumferential face 20a of the rotating drum 20, or at the downstream side from the top 20t in the rotating direction. This can prevent the uneven deposit distribution of the absorbent body 10 in the circumferential direction Dc. The detail is as follows. Because the rotating drum 20 rotates as mentioned above, the deposit distribution of the absorbent body 3 tends to be thicker on the upstream than on the downstream in the rotating direction. Concerning this point, if the lower end 36d of the lower sliding plate 36 is positioned as mentioned above, the landing position of the SAP on the rotating drum 20 is on the downstream side in the rotating direction from the top 20t of the outer circumferential face 20a of the rotating drum 20, the SAP being scattered from the lower end 36d. Because of inclination of the outer circumferential face 20a towards the downstream side, the SAP which has landed is more likely to flow downstream, which results in preventing an excess deposit on the upstream side of the depression 21a (21b) of the mold 21.

It is preferable that, as shown in FIG. 4A, on the downstream side of the sliding direction of the lower sliding plate 36, a wall is not arranged with which the SAP that falls from the sliding plate 36 comes into contact before the SAP lands on the surface sheet 5 located on the rotating drum 20. In this case, while transferring the SAP from the lower sliding plate 36 to the surface sheet 5 located on the rotating drum 20, the state of the SAP is not disturbed in which the SAP is distributed evenly by sliding on the lower sliding plate 36, and the SAP falls from the lower end 36d of the sliding plate 36 and lands on the surface sheet 5. This makes it possible to achieve the even deposit distribution of the absorbent body 3 in the width direction.

Figure 6A:
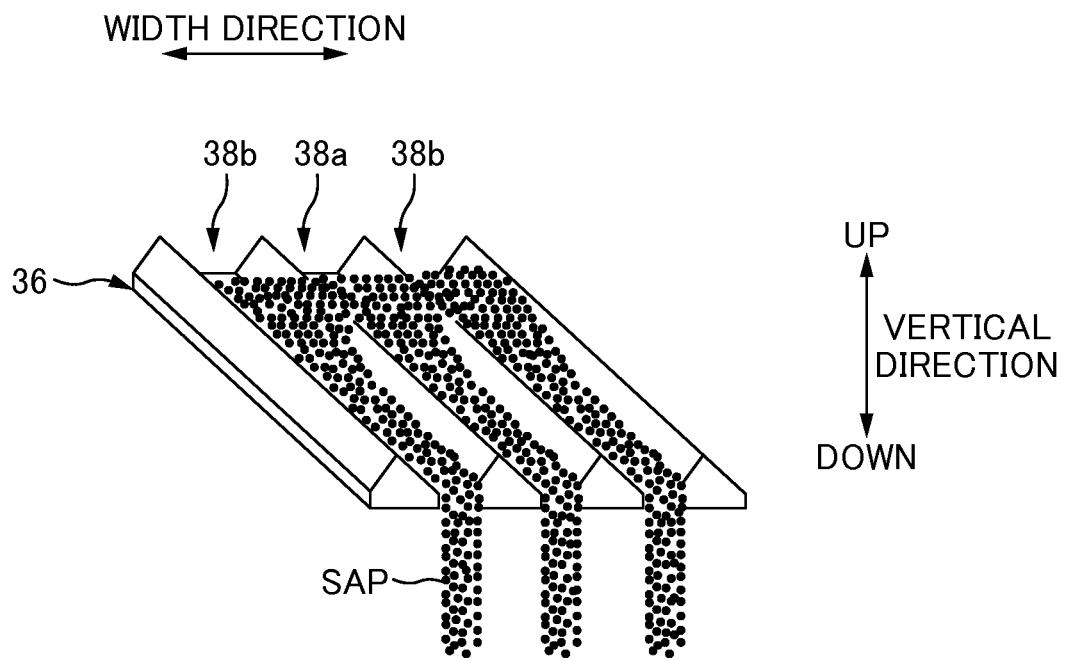
FIGS. 6A and 6B are respectively perspective views of the lower sliding plate 36 according to the modified examples.

FIG. 6A is a perspective view of lower sliding plate 36 of the modified example of. In the foregoing example, the upper surface of sliding plate 36 is a flat surface. However, in the modified example, on the upper surface of the sliding plate 36, a plurality of guiding grooves 38b, 38a, 38b extending along the sliding direction is formed lined up in the width direction. Each of the guiding grooves 38b, 38a, 38b is formed respectively corresponding to each depression 21b, 21a, 21b of the mold 21 (see FIG. 3). That is, the central position of each guiding grooves 38b, 38a, 38b in the width direction is arranged such that the guiding grooves respectively are within the corresponding depressions 21b, 21a, 21b. Therefore, the SAP is guided by each of the guiding grooves 38b, 38a, 38b and is definitely led to the depressions 21b, 21a, 21b of the mold 21, which results in preventing effectively falling of the SAP outside each of the depressions 21b, 21a, 21b.

Figure 6B:
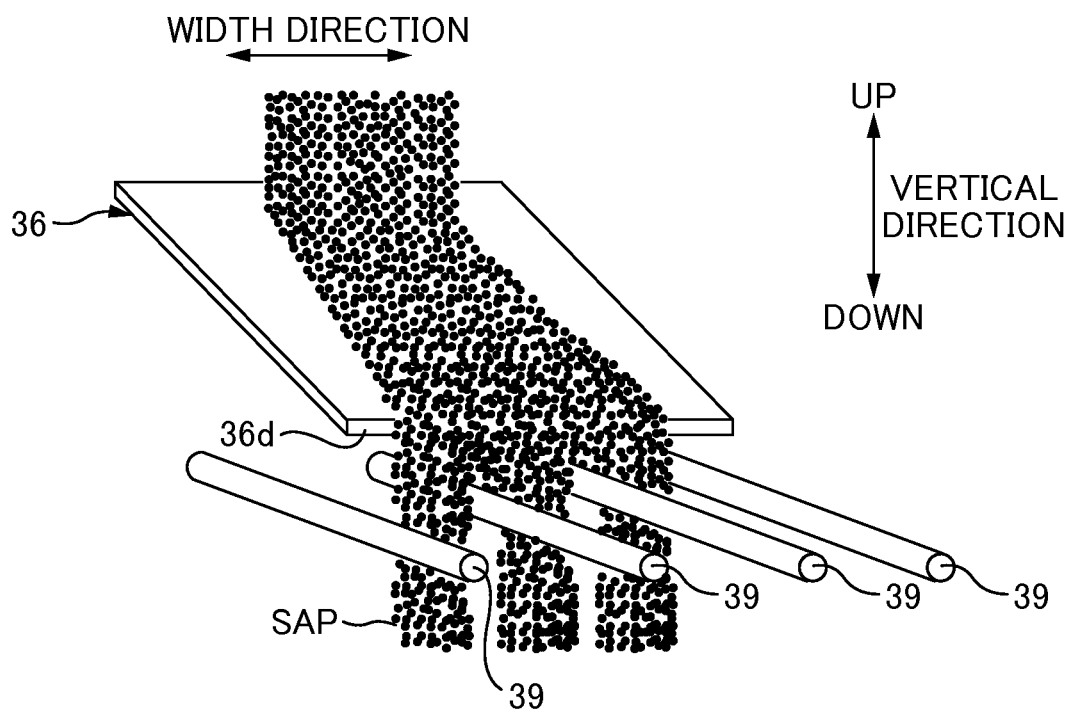

Instead of the foregoing guiding grooves 38b, 38a, 38b, it is possible to arrange below the lower end 36d of the sliding plate rod-shaped guide members 39 which are located along the circumferential direction Dc, and to lead the SAP to each of the depressions 21b, 21a, 21b of the mold 21, as shown in the perspective view of FIG. 6B. In this case, the guide members 39 are arranged, with respect to the width direction, at a position where the depressions 21b, 21a, 21b of the mold 21 do not exist.

In the final joining step, as shown in FIG. 2, the surface sheet 5 and back face sheet 7 are joined with placing the back face sheet 7 over the surface sheet 5 on which the absorbent body 3 is deposited. More specifically, at a position on the more downstream side than the installed position of the foregoing SAP-supply device 30 in the rotating direction of the rotating drum 20, the back face sheet 7 is supplied by continuously rolling out from a reel (not shown) and is placed over the surface sheet 5. Onto this back face sheet 7, hot-melt adhesive is applied, in advance, by an adhesive-applying device 50 in strips along the circumferential direction Dc, lined up at a regular interval in the width direction. Thereby, the back face sheet 7 adheres to the surface sheet 5, and a continuous body of the foregoing absorbent main body 1 is formed.

Thereafter, the continuous body of the absorbent main body 1 is removed from the outer circumferential face 20a of the rotating drum 20 at a predetermined position on the rotating drum 20, and is transferred to a pair of upper and lower heat sealing rollers 60a, 60b. On an outer circumferential face of the upper heat sealing roller 60a, depressions corresponding to the depositing pattern are formed; thereby the surface sheet 5 and back face sheet 7 are hot-melt bonded, except areas of the absorbent main body 1 where the island-shaped deposited portions 3a, 3b of the absorbent body 3 are located.

It is also possible that an adhesive-applying device 70 shown in FIG. 2 applies the hot-melt adhesive onto the surface sheet 5 in the foregoing depositing pattern, before wrapping the surface sheet 5 around the rotating drum 20. In this case, the SAP which is led to the depressions 21b, 21a, 21b of the mold 21 can be fixed quickly and securely to portions of the surface sheet 5 which are at the same position as the depressions.

In this regard, the foregoing reel, the adhesive-applying device 50, 70, and the heat sealing rollers 60a, 60b etc correspond to a joining mechanism.

OTHER EMBODIMENTS

Embodiments of the present invention have been described as above, however the present invention is not limited to these embodiments and the following variations are also possible.

In the foregoing embodiment, concerning all sliding plates 36, the sliding directions of a pair of the sliding plates 36, 36 adjacent in the up-and-down direction are opposite from each other. However, the invention is not limited thereto. Indeed, it is sufficient that at least one sliding plate 36 of a plurality of sliding plates 36 makes the SAP reverse its sliding direction and slide, the SAP falling from the adjacent sliding plate 36 above it. Among a plurality of pairs of the sliding plates 36, 36 adjacent in the up-and-down direction, there may be some pairs which do not make the SAP reverse its sliding direction.

In the foregoing embodiment, the rotating drum 20 is provided as a mold member. However, the invention is not limited thereto. For example, it is possible to use a belt of a belt conveyor as a mold member, to form the molds 21 in a depressed shape on the belt, and to move the belt along a predetermined path.

In the foregoing embodiment, a direction in which the discharge opening 34a of the SAP-discharging pipe 34 is facing is not described in detail. As shown in FIG. 4A, the discharge opening 34a is preferably facing, not vertically below, to an upper edge 36d of the uppermost sliding plate 36 which has to directly receive the SAP discharged by the SAP-discharging pipe 34. This makes it possible to ensure long sliding-path length of the SAP on the sliding plates 36. Therefore, the evenness of the distribution of the SAP increases in the width direction.

In the foregoing embodiment, the SAP is provided as a liquid-absorbent particle. However, the invention is not limited to superabsorbent polymer as long as a liquid-absorbent particle is a particle having a property to keep absorbed liquid by swelling etc.

In the foregoing embodiment, three of sliding plates 36 are included. However, the invention is not limited thereto as long as a plurality of the sliding plates 36 are included.

In the foregoing embodiment, the case where the mold 21 has a bottom section on which a plurality of suction holes are formed is provided. However, the invention is not limited thereto. For example, the mold 21 does not have to have the bottom section; in other words, the mold 21 may be one through hole that is formed completely through the outer circumferential face 20a of the rotating drum 20 in the thickness direction. In this way, the mold 21 itself may be a suction hole. As a specific example of the foregoing bottom section of the mold 21, a mesh plate such as a woven wire cloth etc can be provided.

In the foregoing embodiment, nonwoven fabric made of synthetic fiber is provided as an example of materials of the surface sheet 5. However, the invention is not limited thereto as long as materials have air-permeability. For example, tissue paper, sheet-like pulverized pulp or the like can be employed.

In the foregoing embodiment, nonwoven fabric made of synthetic fiber is provided as an example of materials of the back face sheet 7. However, the invention is not limited thereto. For example, tissue paper, sheet-like pulverized pulp or the like can be employed.

REFERENCE SIGNS LIST

1 absorbent main body (composite sheet), 3 absorbent body, 3a deposited portion, 3b deposited portion, 5 surface sheet (first sheet), 7 back face sheet (second sheet), 10 manufacturing apparatus, 20 rotating drum (mold member), 20a outer circumferential face (surface), 20t top, 21 mold, 21a depression, 21b depression, 22u edge on upstream side, 30 SAP-supply device (liquid-absorbent-particle-supply mechanism), 31 box member, 31c ceiling, 31d lower end, 31e wall on upstream side, 31f wall on downstream side, 31s side wall, 31u wall on upper surface side, 32 air-inlet opening, 34 SAP-discharging pipe (discharging member), 34a discharge opening, 36 sliding plate (slope member), 36d lower end (downstream end, upstream end), 36s both edges, 36u upper edge (downstream end, upstream end), 37 vertical wall, 38a guiding groove, 38b guiding groove, 39 guide member, 50 adhesive-applying device, 60a heat sealing roller, 60b heat sealing roller, 70 adhesive-applying device, C20 horizontal axis, C34 pipe axis.

The invention claimed is:

1. A manufacturing method for a composite sheet formed by sandwiching an absorbent body that absorbs liquid between a first sheet and a second sheet, comprising:
    conveying the first sheet with abutting a mold member on a surface of the mold member, the first sheet being continuous in a first direction, the mold member including a mold formed on the surface in a depressed shape and moving along the first direction perpendicular to a width direction of the surface;
    forming the absorbent body using a procedure in which a liquid-absorbent particle falls towards the first sheet abutting the surface and the liquid-absorbent particle is deposited on a corresponding portion of the first sheet to the mold by suction from a suction hole of the mold; and
    joining the second sheet and the first sheet with placing the second sheet over the first sheet, the first sheet having the absorbent body that is deposited thereon, the second sheet being continuously transported in the first direction, wherein
    in the forming, a plurality of slope members having a slope is included in an up-and-down direction,
    a height of an upstream end of the slope and a height of a downstream end of the slope are different in the first direction,
    while the liquid-absorbent particle successively slides a slope of the plurality of slope members, the liquid-absorbent particle is distributed in the width direction and falls on the first sheet located on the mold member,
    at least one slope member of the plurality of slope members makes the liquid-absorbent particle reverse its sliding direction and slide, the liquid-absorbent particle falling from a slope member adjacent above the one slope member, wherein
in the forming, a box member that forms a partitioned space together with the surface is included,
the plurality of slope members are housed in the box member,
a discharging member that discharges the liquid-absorbent particles is housed in the box member above the plurality of slope members, and
the plurality of slope members each have opposite ends in the width direction that are fixed on walls of the box member.

2. A manufacturing method for a composite sheet according to claim 1, wherein
three or more of the slope members are included, and
concerning all of the slope members, sliding directions of slope members adjacent in the up-and-down direction are opposite from each other.

3. A manufacturing method for a composite sheet according to claim 1, wherein
the mold of the mold member is formed at a predetermined interval in the first direction,
a lowermost slope member, of the plurality of slope members, drops the liquid-absorbent particle towards the first sheet located on the mold member,
in terms of the component along a horizontal direction, a sliding direction of the lowermost slope member is the same as a moving direction in which the mold member is moving at a landing position of the liquid-absorbent particle on the first sheet.

4. A manufacturing method for a composite sheet according to claim 1, wherein
the mold member is a rotating drum continuously rotating in a rotating direction that is one direction of circumferential directions and is the first direction,
the rotating drum transports the first sheet with wrapping the sheet around an outer circumferential face at a predetermined wrapping angle, the outer circumferential face serving as the surface,
the mold is formed in a depressed shape on the outer circumferential face at a regular interval in the rotating direction,
a lower end of the lowermost slope member of the plurality of slope members is positioned, in the horizontal direction, at a top of the outer circumferential face of the rotating drum, or on a downstream side from the top in the rotating direction.

5. A manufacturing method for a composite sheet according to claim 1, wherein
a slope of a slope member that receives the liquid-absorbent particle falling from a slope member adjacent above that slope member is arranged astride a lower end of the adjacent slope member in the first direction.

6. A manufacturing method for a composite sheet according to claim 1, wherein
on a slope of the lowermost slope member of the plurality of slope members, a plurality of guiding grooves along the sliding direction are formed lined up in the width direction,
a position of a lower end of the guiding groove in the width direction is aligned with the mold.

7. A manufacturing apparatus for a composite sheet formed by sandwiching an absorbent body that absorbs liquid between a first sheet and a second sheet, comprising:
a mold member that includes a mold formed on a surface in a depressed shape, that moves along a first direction perpendicular to a width direction of the surface, and that conveys the first sheet with the first sheet abutting on the surface, the first sheet being continuous in the first direction;
a liquid-absorbent-particle-supply mechanism that drops and supplies the liquid-absorbent particle towards the first sheet abutting the surface;
a suction mechanism that sucks air from a suction hole in the mold in order to form the absorbent body by depositing the liquid-absorbent particle on a corresponding portion of the first sheet to the mold; and
a joining mechanism that places the second sheet over the first sheet on which the absorbent body is deposited and joins the sheets, the second sheet being continuously transported along the first direction, wherein
the liquid-absorbent-particle-supply mechanism includes in an up-and-down direction a plurality of slope members having a slope,
a height of an upstream end of the slope and a height of a downstream end of the slope are different from each other in the first direction,
while the liquid-absorbent particle successively slides a slope of the plurality of slope members, the liquid-absorbent particle is distributed in the width direction and falls onto the first sheet on the mold member,
at least one slope member of the plurality of slope members makes the liquid-absorbent particle reverse its sliding direction and slide, the liquid-absorbent particle falling from a slope member adjacent above the one slope member,
wherein
a box member that forms a partitioned space together with the surface is provided,
the plurality of slope members are housed in the box member,
a discharging member that discharges the liquid-absorbent particles is housed in the box member above the plurality of slope members, and
the plurality of slope members each have opposite ends in the width direction that are fixed on walls of the box member.

* * * * *

UNITED STATES PATENT AND TRADEMARK OFFICE
CERTIFICATE OF CORRECTION

PATENT NO. : 8,597,458 B2
APPLICATION NO. : 13/258977
DATED : December 3, 2013
INVENTOR(S) : Taniguchi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 171 days.

Signed and Sealed this
Twenty-second Day of September, 2015

Michelle K. Lee
*Director of the United States Patent and Trademark Office*